United States Patent
Yang et al.

(10) Patent No.: US 10,973,916 B2
(45) Date of Patent: Apr. 13, 2021

(54) BISPECIFIC ANTIBODY TARGETING HUMAN P185 AND VASCULAR ENDOTHELIAL GROWTH FACTOR AND APPLICATION THEREOF

(71) Applicant: Sun-Bio Medical Device Co., Ltd., Tokyo (JP)

(72) Inventors: Yang Yang, Shanghai (CN); Wei Yin, Wuhan (CN)

(73) Assignee: Sun-Bio Medical Device Co., Ltd., Tokyo (JP)

( * ) Notice: Subject to any disclaimer, the term of this patent is extended or adjusted under 35 U.S.C. 154(b) by 462 days.

(21) Appl. No.: 15/854,645

(22) Filed: Dec. 26, 2017

(65) Prior Publication Data

US 2019/0091331 A1 Mar. 28, 2019

(30) Foreign Application Priority Data

Sep. 22, 2017 (CN) .......................... 201710867265.5

(51) Int. Cl.
| | |
|---|---|
| *C07K 16/22* | (2006.01) |
| *C07K 16/32* | (2006.01) |
| *A61K 39/395* | (2006.01) |
| *A61P 35/00* | (2006.01) |
| *C12N 15/79* | (2006.01) |

(52) U.S. Cl.
CPC ........ *A61K 39/39558* (2013.01); *A61P 35/00* (2018.01); *C07K 16/22* (2013.01); *C07K 16/32* (2013.01); *C12N 15/79* (2013.01); *C07K 2317/31* (2013.01); *C07K 2317/32* (2013.01); *C07K 2317/622* (2013.01)

(58) Field of Classification Search
CPC ........ A61K 39/39558; A61K 2039/505; C07K 16/32; C07K 16/22; C07K 2317/31; C07K 2317/32; C07K 2317/622; C07K 16/40; C07K 16/468; C07K 2317/51; C07K 2317/515; C07K 2317/92; A61P 35/00; C12N 15/79
See application file for complete search history.

(56) References Cited

U.S. PATENT DOCUMENTS

| | | | |
|---|---|---|---|
| 8,592,149 B2 * | 11/2013 | Ramakrishnan ... | C07K 16/2887 435/6.1 |
| 2010/0260668 A1 | 10/2010 | Ghayur et al. | |
| 2015/0044216 A1 * | 2/2015 | Wu .................... | A61K 47/6879 424/136.1 |
| 2015/0322165 A1 * | 11/2015 | Cheong ................. | C07K 16/32 424/136.1 |

FOREIGN PATENT DOCUMENTS

| | | |
|---|---|---|
| CN | 104744592 A | 7/2015 |
| CN | 106084062 A | 11/2016 |
| WO | WO 99/57134 A1 | 11/1999 |
| WO | WO 2010/027981 A1 | 3/2010 |
| WO | WO 2012/145507 A2 | 10/2012 |
| WO | WO 2016/008975 A1 | 1/2016 |

OTHER PUBLICATIONS

Pegram et al., Combined Biological Therapy of Breast Cancer Using Monoclonal Antibodies Directed Against HER2/neu Protein and Vascular Endothelial Growth Factor, Seminars in Oncology, vol. 29, No. 3, Suppl 11 Jun. 2002: pp. 29-37 (Year: 2002).*
Xiao-Feng Le et al., "Specific blockade of VEGF and HER2 pathwakys results in greater growth inhibition of breast cancer xenografts that overexpress HER2," Cell Cycle, vol. No. 7, No. 23, pp. 3747-3758 (Dec. 1, 2008).
Roland Kontermann, "Dual targeting strategies with bispecific antibodies," mAbs, vol. No. 4, Iss. No. 2, pp. 182-197 (Mar. 1, 2012).
Spiess, Christoph et al., "Alternative molecular formats and therapeutic applications for bispecific antibodies," Molecular Immunology, Pergamon, GB, vol. No. 67, No. 2, pp. 95-106 (Jan. 27, 2015).
Bostrom, Jenny et al., "Variants of the antibody herceptin that interact with HER2 and VEGF at the antigen binding site," Science, vol. No. 323, No. 5921, pp. 1610-1614 (Mar. 20, 20009).

* cited by examiner

*Primary Examiner* — Brad Duffy
*Assistant Examiner* — Cheom-Gil Cheong
(74) *Attorney, Agent, or Firm* — Mei & Mark LLP; Manni Li (57) ABSTRACT

A bispecific antibody that simultaneously targets humanized p185 and VEGF, consisting of the four peptide chains: two identical antibody light chains that are the light chains of the antibody that identify the epitope or antigen of p185, and two identical antibody heavy chains that have the amino acid sequence of a recombinant antibody from N- to C-terminus, a light chain sequence of the antibody that recognizes the p185 epitope or the antigen; a constant heavy chain region; a flexible short peptide sequence; and either a single-stranded variable region sequence (ScFv) of anti-VEGF antibody which recognizes the VEGF epitope or antigen, or a receptor domain sequence that binds to VEGF. The bispecific antibody has the ability to bind p185 and VEGF at the same time, inhibits the proliferation of tumor cells, and promotes the expression of IFN-γ by T lymphocytes; it may be applied as anti-tumor antibody drug.

1 Claim, 4 Drawing Sheets
Specification includes a Sequence Listing.

SEQUENCE LISTING

```
<160> NUMBER OF SEQ ID NOS: 6

<210> SEQ ID NO 1
<211> LENGTH: 214
<212> TYPE: PRT
<213> ORGANISM: Artificial sequence
<220> FEATURE:
<223> OTHER INFORMATION: light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 2
<211> LENGTH: 710
<212> TYPE: PRT
<213> ORGANISM: Artificial sequence
<220> FEATURE:
<223> OTHER INFORMATION: Recombinant heavy chain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

-continued

His Asn Ala Lys Thr Lys Pro Arg Glu Glu Gln Tyr Asn Ser Thr Tyr
290             295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Gly Gly Gly Ser Gly Gly Gly Gly Ser Gly Gly Gly Gly Ser
450                 455                 460

Glu Val Gln Leu Val Glu Ser Gly Gly Gly Leu Val Gln Pro Gly Gly
465                 470                 475                 480

Ser Leu Arg Leu Ser Cys Ala Ala Ser Gly Tyr Thr Phe Thr Asn Tyr
                485                 490                 495

Gly Met Asn Trp Val Arg Gln Ala Pro Gly Lys Gly Leu Glu Trp Val
                500                 505                 510

Gly Trp Ile Asn Thr Tyr Thr Gly Glu Pro Thr Tyr Ala Ala Asp Phe
            515                 520                 525

Lys Arg Arg Phe Thr Phe Ser Leu Asp Thr Ser Lys Ser Thr Ala Tyr
            530                 535                 540

Leu Gln Met Asn Ser Leu Arg Ala Glu Asp Thr Ala Val Tyr Tyr Cys
545                 550                 555                 560

Ala Lys Tyr Pro His Tyr Tyr Gly Ser Ser His Trp Tyr Phe Asp Val
                565                 570                 575

Trp Gly Gln Gly Thr Leu Val Thr Val Ser Ser Gly Gly Gly Ser Gly
                580                 585                 590

Gly Gly Ser Gly Gly Gly Ser Gly Gly Gly Ser Asp Ile Gln Met Thr
            595                 600                 605

Gln Ser Pro Ser Ser Leu Ser Ala Ser Val Gly Asp Arg Val Thr Ile
610                 615                 620

Thr Cys Ser Ala Ser Gln Asp Ile Ser Asn Tyr Leu Asn Trp Tyr Gln
625                 630                 635                 640

Gln Lys Pro Gly Lys Ala Pro Lys Val Leu Ile Tyr Phe Thr Ser Ser
                645                 650                 655

Leu His Ser Gly Val Pro Ser Arg Phe Ser Gly Ser Gly Ser Gly Thr
            660                 665                 670

Asp Phe Thr Leu Thr Ile Ser Ser Leu Gln Pro Glu Asp Phe Ala Thr
            675                 680                 685

Tyr Tyr Cys Gln Gln Tyr Ser Thr Val Pro Trp Thr Phe Gly Gln Gly
690                 695                 700

Thr Lys Val Glu Ile Lys

-continued

```
705                 710

<210> SEQ ID NO 3
<211> LENGTH: 710
<212> TYPE: PRT
<213> ORGANISM: Artificial sequence
<220> FEATURE:
<223> OTHER INFORMATION: Recombinant heavy chain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
```

```
                355                 360                 365
Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Gly Ser Gly Gly Gly Gly Ser
    450                 455                 460

Asp Ile Gln Met Thr Gln Ser Pro Ser Ser Leu Ser Ala Ser Val Gly
465                 470                 475                 480

Asp Arg Val Thr Ile Thr Cys Ser Ala Ser Gln Asp Ile Ser Asn Tyr
                485                 490                 495

Leu Asn Trp Tyr Gln Gln Lys Pro Gly Lys Ala Pro Lys Val Leu Ile
            500                 505                 510

Tyr Phe Thr Ser Ser Leu His Ser Gly Val Pro Ser Arg Phe Ser Gly
        515                 520                 525

Ser Gly Ser Gly Thr Asp Phe Thr Leu Thr Ile Ser Ser Leu Gln Pro
    530                 535                 540

Glu Asp Phe Ala Thr Tyr Tyr Cys Gln Gln Tyr Ser Thr Val Pro Trp
545                 550                 555                 560

Thr Phe Gly Gln Gly Thr Lys Val Glu Ile Lys Gly Gly Gly Ser Gly
                565                 570                 575

Gly Gly Ser Gly Gly Gly Ser Gly Gly Gly Ser Glu Val Gln Leu Val
            580                 585                 590

Glu Ser Gly Gly Gly Leu Val Gln Pro Gly Gly Ser Leu Arg Leu Ser
        595                 600                 605

Cys Ala Ala Ser Gly Tyr Thr Phe Thr Asn Tyr Gly Met Asn Trp Val
    610                 615                 620

Arg Gln Ala Pro Gly Lys Gly Leu Glu Trp Val Gly Trp Ile Asn Thr
625                 630                 635                 640

Tyr Thr Gly Glu Pro Thr Tyr Ala Ala Asp Phe Lys Arg Arg Phe Thr
                645                 650                 655

Phe Ser Leu Asp Thr Ser Lys Ser Thr Ala Tyr Leu Gln Met Asn Ser
            660                 665                 670

Leu Arg Ala Glu Asp Thr Ala Val Tyr Tyr Cys Ala Lys Tyr Pro His
        675                 680                 685

Tyr Tyr Gly Ser Ser His Trp Tyr Phe Asp Val Trp Gly Gln Gly Thr
    690                 695                 700

Leu Val Thr Val Ser Ser
705                 710

<210> SEQ ID NO 4
<211> LENGTH: 653
<212> TYPE: PRT
<213> ORGANISM: Artificial sequence
<220> FEATURE:
<223> OTHER INFORMATION: Recombinant heavy chain

<400> SEQUENCE: 4

Glu Val Gln Leu Val Glu Ser Gly Gly Gly Leu Val Gln Pro Gly Gly
```

```
  1               5                  10                 15
Ser Leu Arg Leu Ser Cys Ala Ala Ser Gly Phe Asn Ile Lys Asp Thr
            20                  25                 30

Tyr Ile His Trp Val Arg Gln Ala Pro Gly Lys Gly Leu Glu Trp Val
            35                  40                 45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                 80

Leu Gln Met Asn Ser Leu Arg Ala Glu Asp Thr Ala Val Tyr Tyr Cys
            85                  90                 95

Ser Arg Trp Gly Gly Asp Gly Phe Tyr Ala Met Asp Tyr Trp Gly Gln
            100                 105                110

Gly Thr Leu Val Thr Val Ser Ser Ala Ser Thr Lys Gly Pro Ser Val
            115                 120                125

Phe Pro Leu Ala Pro Ser Ser Lys Ser Thr Ser Gly Gly Thr Ala Ala
            130                 135                140

Leu Gly Cys Leu Val Lys Asp Tyr Phe Pro Glu Pro Val Thr Val Ser
145                 150                 155                160

Trp Asn Ser Gly Ala Leu Thr Ser Gly Val His Thr Phe Pro Ala Val
            165                 170                175

Leu Gln Ser Ser Gly Leu Tyr Ser Leu Ser Ser Val Val Thr Val Pro
            180                 185                190

Ser Ser Ser Leu Gly Thr Gln Thr Tyr Ile Cys Asn Val Asn His Lys
            195                 200                205

Pro Ser Asn Thr Lys Val Asp Lys Lys Val Glu Pro Lys Ser Cys
            210                 215                220

Asp Lys Thr His Thr Cys Pro Pro Cys Pro Ala Pro Glu Leu Leu Gly
225                 230                 235                240

Gly Pro Ser Val Phe Leu Phe Pro Pro Lys Pro Lys Asp Thr Leu Met
            245                 250                255

Ile Ser Arg Thr Pro Glu Val Thr Cys Val Val Val Asp Val Ser His
            260                 265                270

Glu Asp Pro Glu Val Lys Phe Asn Trp Tyr Val Asp Gly Val Glu Val
            275                 280                285

His Asn Ala Lys Thr Lys Pro Arg Glu Glu Gln Tyr Asn Ser Thr Tyr
            290                 295                300

Arg Val Val Ser Val Leu Thr Val Leu His Gln Asp Trp Leu Asn Gly
305                 310                 315                320

Lys Glu Tyr Lys Cys Lys Val Ser Asn Lys Ala Leu Pro Ala Pro Ile
            325                 330                335

Glu Lys Thr Ile Ser Lys Ala Lys Gly Gln Pro Arg Glu Pro Gln Val
            340                 345                350

Tyr Thr Leu Pro Pro Ser Arg Asp Glu Leu Thr Lys Asn Gln Val Ser
            355                 360                365

Leu Thr Cys Leu Val Lys Gly Phe Tyr Pro Ser Asp Ile Ala Val Glu
            370                 375                380

Trp Glu Ser Asn Gly Gln Pro Glu Asn Tyr Lys Thr Thr Pro Pro
385                 390                 395                400

Val Leu Asp Ser Asp Gly Ser Phe Phe Leu Tyr Ser Lys Leu Thr Val
            405                 410                415

Asp Lys Ser Arg Trp Gln Gln Gly Asn Val Phe Ser Cys Ser Val Met
            420                 425                430
```

-continued

His Glu Ala Leu His Asn His Tyr Thr Gln Lys Ser Leu Ser Leu Ser
            435                 440                 445

Pro Gly Gly Gly Ser Gly Gly Gly Ser Gly Gly Gly Ser
    450                 455                 460

Ser Asp Thr Gly Arg Pro Phe Val Glu Met Tyr Ser Glu Ile Pro Glu
465                 470                 475                 480

Ile Ile His Met Thr Glu Gly Arg Glu Leu Val Ile Pro Cys Arg Val
                485                 490                 495

Thr Ser Pro Asn Ile Thr Val Thr Leu Lys Lys Phe Pro Leu Asp Thr
            500                 505                 510

Leu Ile Pro Asp Gly Lys Arg Ile Ile Trp Asp Ser Arg Lys Gly Phe
        515                 520                 525

Ile Ile Ser Asn Ala Thr Tyr Lys Glu Ile Gly Leu Leu Thr Cys Glu
    530                 535                 540

Ala Thr Val Asn Gly His Asp Val Val Leu Ser Pro Ser His Gly Ile
545                 550                 555                 560

Glu Leu Ser Val Gly Glu Lys Leu Val Leu Asn Cys Thr Ala Arg Thr
                565                 570                 575

Glu Leu Asn Val Gly Ile Asp Phe Asn Trp Glu Tyr Pro Ser Ser Lys
            580                 585                 590

His Gln His Lys Lys Leu Val Asn Arg Asp Leu Lys Thr Gln Ser Gly
        595                 600                 605

Ser Glu Met Lys Lys Phe Leu Ser Thr Leu Thr Ile Asp Gly Val Thr
    610                 615                 620

Arg Ser Asp Gln Gly Leu Tyr Thr Cys Ala Ala Ser Ser Gly Leu Met
625                 630                 635                 640

Thr Lys Lys Asn Ser Thr Phe Val Arg Val His Glu Lys
                645                 650

<210> SEQ ID NO 5
<211> LENGTH: 676
<212> TYPE: PRT
<213> ORGANISM: Artificial sequence
<220> FEATURE:
<223> OTHER INFORMATION: Recombinant heavy chain

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Gly Ser Gly Gly Gly Gly Ser
450                 455                 460

Ser Asp Thr Gly Arg Pro Phe Val Glu Met Tyr Ser Glu Ile Pro Glu
465                 470                 475                 480

Ile Ile His Met Thr Glu Gly Arg Glu Leu Val Ile Pro Cys Arg Val
                485                 490                 495

Thr Ser Pro Asn Ile Thr Val Thr Leu Lys Lys Phe Pro Leu Asp Thr
            500                 505                 510

Leu Ile Pro Asp Gly Lys Arg Ile Ile Trp Asp Ser Arg Lys Gly Phe
        515                 520                 525

Ile Ile Ser Asn Ala Thr Tyr Lys Glu Ile Gly Leu Leu Thr Cys Glu
530                 535                 540

Ala Thr Val Asn Gly His Leu Tyr Lys Thr Asn Tyr Leu Thr His Arg
545                 550                 555                 560
```

```
Gln Thr Asn Thr Ile Ile Asp Val Gln Ile Ser Thr Pro Arg Pro Val
            565                 570                 575

Lys Leu Leu Arg Gly His Thr Leu Val Leu Asn Cys Thr Ala Thr Thr
        580                 585                 590

Pro Leu Asn Thr Arg Val Gln Met Thr Trp Ser Tyr Pro Asp Glu Lys
        595                 600                 605

Asn Lys Arg Ala Ser Val Arg Arg Arg Ile Asp Gln Ser Asn Ser His
    610                 615                 620

Ala Asn Ile Phe Tyr Ser Val Leu Thr Ile Asp Lys Met Gln Asn Lys
625                 630                 635                 640

Asp Lys Gly Leu Tyr Thr Cys Arg Val Arg Ser Gly Pro Ser Phe Lys
                645                 650                 655

Ser Val Asn Thr Ser Val His Ile Tyr Asp Lys Ala Phe Ile Thr Val
            660                 665                 670

Lys His Arg Lys
        675

<210> SEQ ID NO 6
<211> LENGTH: 15
<212> TYPE: PRT
<213> ORGANISM: Artificial sequence
<220> FEATURE:
<223> OTHER INFORMATION: Flexible peptide

<400> SEQUENCE: 6

Gly Gly Gly Gly Ser Gly Gly Gly Gly Ser Gly Gly Gly Gly Ser
1               5                   10                  15
```

BISPECIFIC ANTIBODY TARGETING HUMAN P185 AND VASCULAR ENDOTHELIAL GROWTH FACTOR AND APPLICATION THEREOF

CROSS-REFERENCE TO RELATED APPLICATIONS

The subject application claims priority on Chinese application no. 201710867265.5 filed on Sep. 22, 2017. The contents and subject matter of the Chinese priority application are incorporated herein by reference.

TECHNICAL FIELD

The present invention relates to biomedicine, particularly, an antibody that simultaneously targets human p185 and vascular endothelial growth factor (VEGF) and the application thereof.

BACKGROUND OF THE INVENTION

Malignant tumor is the neoplasma induced by tumorigenic factors and characterized by growth of local tissue cells. In 2015, the number of newly developed cancer in China reached 4,292,000 cases, which seriously affected human health.

Tumor molecular biology studies have confirmed that abnormal activation of the human epidermal growth factor receptor 2 gene (HER2), Myc gene, and other oncogenes, which causes disorders of cell signaling pathway and thus leads to cell proliferation, is the molecular mechanism of tumorigenesis. HER2 is a member of the epidermal growth factor receptor (EGFR) family and locates on human chromosome 17q21. HER2 encodes a transmembrane protein p185 consisting of 1255 amino acids with tyrosine protein kinase activity. P185 consists of extracellular ligand-binding domain, single-stranded transmembrane region, and intracellular protein tyrosine kinase region (amino acids 720-987). The overactivated p185 protein plays a critical role in promoting cell proliferation through activating the membrane receptor tyrosine protein kinase signaling pathway (Ras/Raf/MAPK), phosphatidylinositol 3-kinase (PI3K/AKT) signaling pathway, and transcriptional activation (STAT) signaling pathway.

The infinite proliferation of tumor cells consumes a large amount of nutrients. In the initial stage of tumor growth, the infiltration of the surrounding tissue is responsible for providing nutrients that maintain its growth. When the tumor grows to 2.0 mm$^3$, new blood vessels grow into the tumor or the central part of the tumor goes through necrosis due to the lack of nutritional supply. At this situation, the tumor tissue is difficult to continue to grow. Vascular endothelial growth factor (VEGF) secreted by tumor cells is not only an important angiogenic factor but also the strongest and most specific growth factor in tumor angiogenesis. VEGF gene locates at chromosome 6p21.3, is composed of 8 exons and 7 introns. It encodes a dimer glycoprotein. VEGF can increase not only the intracellular $Ca^{2+}$ concentration in endothelial cells but also the permeability of macromolecules of micrangium.

The progress of the research on tumor molecular biology provides a solid scientific basis for the renewal of the anti-cancer drug research and development concept. At present, the focus of anti-tumor drug research and development has shifted from the traditional research and development of cytotoxic drugs to the development of the new generation of anti-tumor drugs which target the key component of dysfunction cell signaling pathway. Target-specific antineoplastic drugs, especially antibody drugs, based on gene expression differences between normal cells and tumor cells, have a high specificity and low toxicity of the therapeutic effect.

SUMMARY OF THE INVENTION

The present invention provides a bispecific antibody against both p185 and VEGF and its clinical use as anti-tumor drugs. The bispecific antibody has the ability to bind p185 and VEGF simultaneously and is capable of inhibiting tumor cell proliferation.

In the present invention, various antibody sequences targeting p185 and VEGF have been synthesized by the molecular biology technique, and based on the antibody affinity and blocking efficiency identified in vitro, recombinant DNA is prepared by the DNA recombination technique and then transfected into mammalian cells to express the bispecific antibody. After purification, identification, and screening, the bispecific antibody which shows the biological effects of simultaneous targeting human p185 and VEGF is thus obtained.

The present invention provides a method for constructing a bispecific antibody that simultaneously targets p185 and VEGF, and the bispecific antibody consists of the following four peptide chains:

(1) two identical antibody light chains, and,
(2) two identical antibody heavy chains;

wherein the antibody light chain is the light chain of the antibody that identifies the epitope or antigen of p185; from the N- to the C-terminus, the amino acid sequence of the heavy chain is:

① light chain sequences that recognize the p185 epitopes or antigens,
② the constant heavy chain region,
③ the flexible peptide sequence,
④ either of the following (a) or (b) sequence: (a) the single-stranded variable region sequence (ScFv) which recognizes a VEGF epitope or antigen, and (b) a receptor domain sequence that binds to VEGF.

In the present invention, the amino acid sequence of the light chain of the antibody that recognizes the p185 epitopes or antigens is preferably the amino acid sequence as shown in SEQ ID NO: 1 in the sequence listing and Table 1.

In the present invention, the amino acid sequence of the heavy chain variable region and the heavy chain constant region is preferably the amino acid sequence of from the first to the 449$^{th}$ position of SEQ ID NO: 2 in the sequence listing and Table 1.

In the present invention, the amino acid sequence of the flexible peptides is preferably the amino acid sequence SEQ ID NO: 6, i.e., GGGGSGGGGSGGGGS.

In the present invention, the single-stranded variable region which recognizes the VEGF epitope or antigen is preferably an amino acid sequence, and the amino acid sequence is the 465$^{th}$ position to the 710$^{th}$ position of SEQ ID NO: 2 or the 465$^{th}$ position to the 710$^{th}$ position of SEQ ID NO: 3 in the sequence listing and Table 1.

In the present invention, the receptor domain which binds to VEGF is preferably an amino acid sequence, and the amino acid sequence is at positions 465 to 653 of SEQ ID NO: 4 or at positions 465 to 676 of SEQ ID NO: 5 in the sequence listing and Table 1.

Preferably, the amino acid sequence of the heavy chain of the recombinant antibody is shown in SEQ ID NO: 2, SEQ ID NO: 3, SEQ ID NO: 4, and SEQ ID NO: 5 in the sequence listing and Table 1.

The present invention provides a bispecific antibody that simultaneously targets human p185 and VEGF and has the biological function that specifically recognizes p185 and VEGF.

The present invention provides a bispecific antibody which simultaneously targets humanized p185 and VEGF. The fusion of the sequence does not affect the secretion of the protein and retains the ability to specifically recognize VEGF and p185 in terms of spatial structure and function.

The present invention also provides a nucleic acid encoding above-mentioned bispecific antibody targeting both p185 and VEGF.

The present invention also provides a recombinant expression vector comprising above-mentioned nucleic acid.

The present invention also provides a recombinant expression transformant comprising above-mentioned recombinant expression vector.

The present invention also provides a method for producing the bispecific antibody comprising the steps of culturing above-mentioned recombinant expression transformant and obtaining the bispecific antibody from the culture.

The present invention also provides the application of the above-mentioned bispecific antibody in the manufacture of a medicament for the treatment or prevention of cancer.

In the present invention, the dosage and the route of administration of the medicament is known to one of skilled in the art, and the type of the tumor is conventional, preferably, including lung cancer, breast cancer, or gastric cancer.

The present invention provides a bispecific antibody that targets and binds to human p185 and VEGF simultaneously, has a high affinity, and is capable of effectively blocking p185 and VEGF proteins at the protein level. The antibody binds both p185 and VEGF proteins, or binds to one protein without affecting the binding of another protein, that is, the ability to bind p185 and VEGF simultaneously. The antibody fills the gap that there is no antibody which simultaneously targets p185 and VEGF. The bispecific antibody inhibits the proliferation of vascular endothelial cells, human lung cancer cells, human breast cancer cells, and human gastric cancer cells. T cell stimulation assay demonstrates that the bispecific antibody promotes the IFN-γ expression by T lymphocytes.

BRIEF DESCRIPTION OF THE FIGURES

FIG. 2 shows that the bispecific antibody of the present invention, having the light chain sequence of SEQ ID NO: 1 and the recombinant heavy chain sequence of SEQ ID NO: 2 that targets human p185 and VEGF, has a high affinity with human p185 and VEGF proteins, among which.

FIG. 3 shows that the bispecific antibody of the present invention, having the light chain sequence of SEQ ID NO: 1 and the recombinant heavy chain sequence of SEQ ID NO: 2 that targets human p185 and VEGF, can effectively recognize human p185 and VEGF proteins, among which.

DETAILED DESCRIPTION OF THE INVENTION

Figure 1:
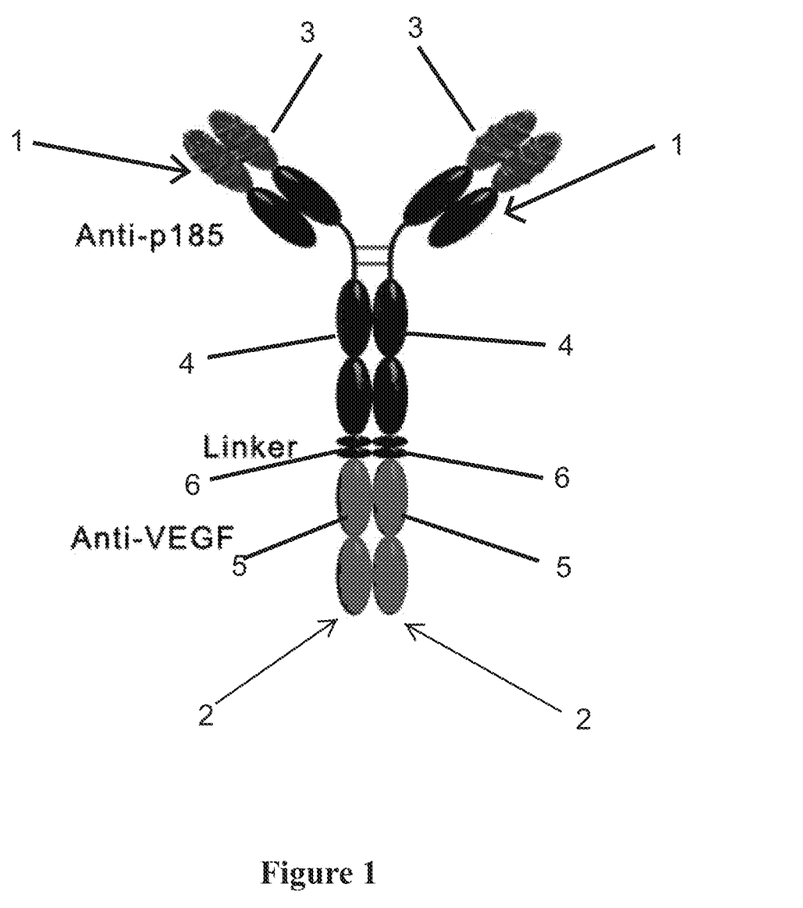
FIG. 1 is a schematic drawing showing the structure of the bispecific antibody that simultaneously targets human p185 and vascular endothelial growth factor.
Figure 2A:
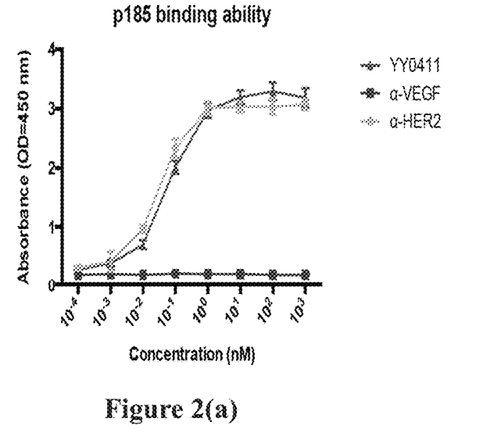
FIG. 2(a) shows the p185 binding ability.
Figure 2B:
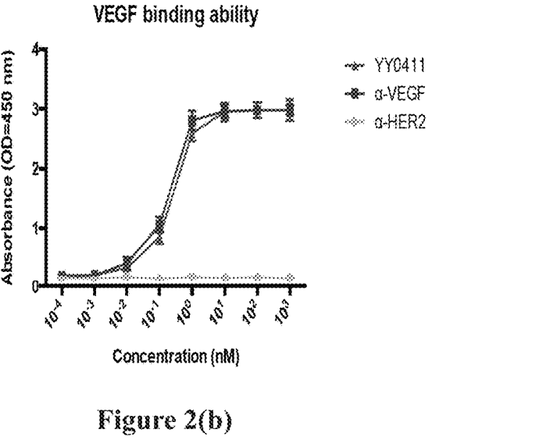
FIG. 2(b) shows the VEGF binding ability.
Figure 2C:
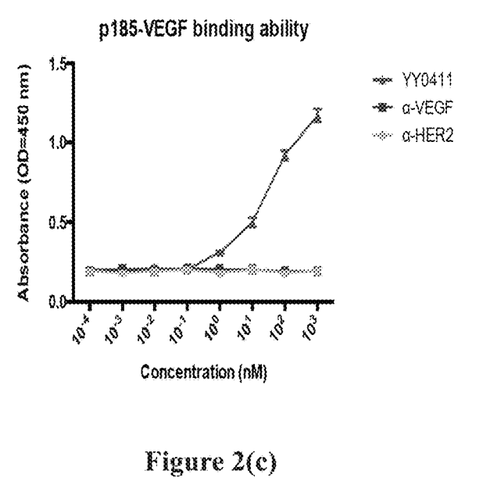
FIG. 2(c) shows the p185-VEGF binding ability.
Figure 2D:
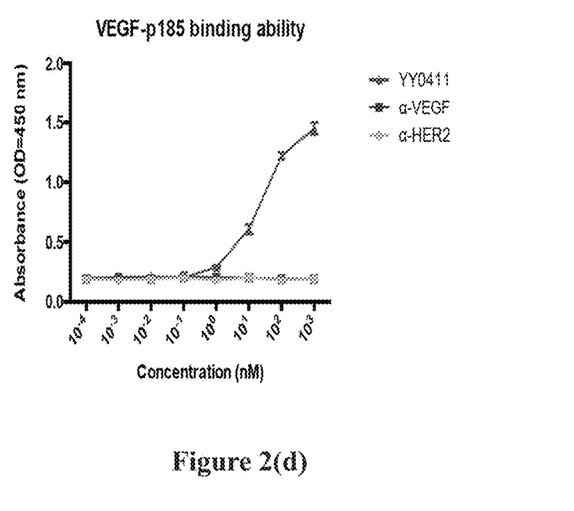
FIG. 2(d) shows the VEGF-p185 binding ability.

The present invention provides a bispecific antibody that simultaneously targets human p185 and VEGF. The bispecific antibody consists of two identical light chains and two identical heavy chains. The structure of the light chain and the recombinant heavy chain are shown in FIG. 1 as follows: a light chain 1 is to identify p185 antigen epitopes or antigen (amino acid sequence shown in Table 1); recombinant heavy chain sequence 2 (amino acid sequence shown in Table 1): the N-terminus is the light chain sequence 3 that recognizes the p185 epitope antibody, followed by the constant heavy chain 4; the C-terminus is the single-stranded variable region sequence (ScFv) 5 which recognizes an VEGF epitope or antigen, or a receptor domain sequence that binds to VEGF. The N-terminus and C-terminus of the recombinant heavy chain are linked by a flexible peptide 6 that is the linker that links the constant heavy chain 4 and the C-terminus single stranded variable region sequence 5 in FIG. 1.

TABLE 1

Amino acid sequences of bispecific antibody targeting both human p185 and VEGF

| Serial Number | Name | Sequence |
|---|---|---|
| SEQ ID NO: 1 | Light chain sequence | DIQMTQSPSSLSASVGDRVTITCRASQDVNTAVAW YQQKPGKAPKLLIYSASFINSGVPSRFSGSRSGTD FTLTISSLQPEDFATYYCQQHYTTPPTFGQGTKVEI KRTVAAPSVFIFPPSDEQLKSGTASVVCLLNNFAP REAKVQWKVDNALQSGNSQESVTEQDSKDSTYS LSSTLTLSKADYEKHKVYACEVTHQGLSSPVTKS FNRGEC |
| SEQ ID NO: 2 | Recombinant heavy chain sequence 1 | EVQLVESGGGLVQPGGSLRLSCAASGFNIKDTYIH WVRQAPGKGLEWVARIYPTNGYTRYADSVKGRF TISADTSKNTAYLQMNSLRAEDTAVYYCSRWGGD GFYAMDYWGQGTLVTVSSASTKGPSVFPLAPSSK STSGGTAALGCLVKDYYPEPVTVSWNSGALTSGV HTFPAVLQSSGLYSLSSVVTYPSSSLGTQTYICNVN HKPSNTKVDKKVEPPKSCDKTHTCPPCPAPELLG GPSVFLFPPKPKDTLMISRTPEVTCVVVDVSHEDP EVKFNWYVDGVEVHNAKTKPREEQYNSTYRVVS VLTVLHQDWLNGKEYKCKVSNKALPAPIEKTISK AKGQPREPVYTLPPSRDELTKNQVSLTCLVKGF YPSDIAVEWESNGQPENNYKTTPPVLDSDGSFFLY SKLTVDKSRWQQGNVFSCSVMHEALHNHYTQKS LSLSPGGGGSGGGGSGGGGSEVQLVESGGGLVQP GGSLRLSCAASGYTFTNYGMNWVRQAPGKGLE WVGWINTYTGEPTYAADFKRRFTFSLDTSKSTAY LQMNSLRAEDTAVYYCAKYPHYYGSSHWYFDV WGQGTLVTVSSGGGSGGGSGGGSGGGSDIQMTQ |

TABLE 1-continued

Amino acid sequences of bispecific antibody targeting both human p185 and VEGF

| Serial Number | Name | Sequence |
|---|---|---|
| | | SPSSLSASVGDRVTITCSASQDISNYLNWYQQKPG KAPKVLIYFTSSLHSGVPSRFSGSGSGTDFTLTISS LQPEDFATYYCQQYSTVPWTFGQGTKVEIK |
| SEQ ID NO: 3 | Recombinant heavy chain sequence 2 | EVQLVESGGGLVQPGGSLRLSCAASGFNIKDTYIH WVRQAPGKGLEWVARIYPTNGYTRYADSVKGRF TISADTSKNTAYLQMNSLRAEDTAVYYCSRWGGD GFYAMDYWGQGTLVTVSSASTKGPSVFPLAPSSK STSGGTAALGCLVKDYFPEPVTVSWNSGALTSG HTFPAVLQSSGLYSLSSVVTVPSSSLGTQTYICNVN HKPSNTKVDKKVEPPKSCDKTHTCPPCPAPELLG GPSVFLFPPKTKDTLMISKTPEVTCVVVDVSHEDP EVKFNWYVDGVEVHNAKTKPREEQYNSTYRVVS VLTVLHQDWLNGKEYKCKVSNKALPAPIEKTISK AKGQPREPQVYTLPPSRDELTKNQVSLTCLVKGF YPSDIAVEWESNGQPENNYKTTPPVLDSDGSFFLY SKLTVDKSRWQQGNVFSCSVMHEALHNHYTQKS LSLSPGGGGSGGGGSGGGGSDIQMTQSPSSLSAS VGDRVTITCSASQDISNYLNWYQQKPGKAPKVLI YFTSSLHSGVPSRFSGSGSGTDFTLTISSLQPEDFAT YYCQQYSTYPWTFGQGTKVEIKGGGGSGGGGSGGG SGGGGSEVQLVESGGGLVQPGGSLRLSCAASGYTF TNYGMNWVRQAPGKGLEWVGWINTYTGEPTYA ADFKRRFTFSLDTSKSTAYLQMNSLRAEDTAVYY CAKYPHYYGSSHWYFDVWCOGILVTVSS |
| SEQ ID NO: 4 | Recombinant heavy chain sequence 3 | EVQLVESGGGLVQPGGSLRLSCAASGFNIKDTYIH WVRQAPGKGLEWVARIYPTNGYTRYADSVKGRF TISADTSKNTAYLQMNSLRAEDTAVYYCSRWGGD GFYAMDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNVN HKPSNTKVDKKVEPPKSCDKTHTCPPCPAPELLG GPSVFLFPPKPKDTLMISRTPEVTCVVVDVSHEDP EVKFNWYVDGVEVHNAKTKPREEQYNSTYRVVS VLTVLHQDWLNGKEYKCKVSNKALPAPIEKTISK AKGQPREPQVYTLPPSRDELTKNQVSLTCLVKGF YPSDIAVEWESNGQPENNYKTTPPVLDSDGSFFLY SKLTVDKSRWQQGNVFSCSVMHEALHNHYTQKS LSLSPGGGGSGGGGSGGGGSSDTGRPFVEMYSEI PEIIHMTEGRELVIPCRVTSPNITVTLKKFPLDTLIP DGKRIIWDSRKGFIISNATYKEIGLLTCEATVNGHD VVLSPSHGIELSVGEKLVLNCTARTELNVGIDFNW EYPSSKHQHKKLVNRDLKTQSGSEMKKFLSTLTI DGVTRSDQGLYTCAASSGLMTKKNSTFVRVHEK |
| SEQ ID NO: 5 | Recombinant heavy chain sequence 4 | EVQLVESGGGLVQPGGSLRLSCAASGFNIKDTYIH WVRQAPGKGLEWVARIYPTNGYTRYADSVKGRF TISADTSKNTAYLQMNSLRAEDTAVYYCSRWGGD GFYAMDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNVN HKPSNTKVDKKVEPPKSCDKTHTCPPCPAPELLG GPSVFLFPPKPKDTLMISRTPEVTCVVVDVSHEDP EVKFNWYVDGVEVHNAKTKPREEQYNSTYRVVS VLTVLHQDWLNGKEYKCKVSNKALPAPIEKTISK AKGQPREPQVYTLPPSRDELTKNQVSLTCLVKGF YPSDIAVEWESNGQPENNYKTTPPVLDSDGSFFLY SKLTVDKSRWQQGNVFSCSVMHEALHNHYTQKS LSLSPGGGGSGGGGSGGGGSSDTGRPFVEMYSEI PEIIHMTEGRELVIPCRVTSPNITVTLKKFPLDTLIP DGKRIIWDSRKGFIISNATYKEIGLLTCEATVNGHL YKTNYLTHRQTNTIIDVQISTPRPVKLLRGHTLVL NCTATTPLNTRVQMTWSYPDEKNKRASVRRRIDQ SNSHANIFYSVLTIDKMQNKDKGLYTCRVRSGPSF KSVNTSVHIYDKAFITVKHRK |

In the present invention, the DNA fragments encoding the anti-p185 antibody, the anti-VEGF antibody, or the domain sequence of binding VEGF are firstly synthesized, respectively. Then, the antibody light chain sequence and the recombinant heavy chain sequence are respectively cloned into the eukaryotic expression vector, pcDNA, through recombinant DNA (overlapping PCR technique); then, it is transfected into 293F or CHO cells. The supernatant is collected 5-7 days after transfection and then purified by affinity chromatography gel column to obtain the bispecific antibody.

The following examples described the invention in further details which are not intended to limit the scope of protection for the invention.

Example 1

The DNA fragments encoding the anti-p185 antibody, the anti-VEGF antibody and the VEGF binding domain are synthesized. Then, the light chain sequence (SEQ ID NO: 1) and the recombinant heavy chain sequence (SEQ ID NO: 2, SEQ ID NO: 3, SEQ ID NO: 4, or SEQ ID NO: 5) are cloned into the eukaryotic expression vector, pcDNA, respectively. The light chain and the heavy chain DNA are mixed at a mass ratio of 2:1. The DNA mixture (4-10 μg) and 40 μL of 2M CaCl$_2$ are added to a total volume of 250 μL with ddH$_2$O. The whole mixture is added into 250 μL 2×HBS (NaCl 16.3 g, KCl 0.74 g. Na$_2$HPO$_4$ 0.214 g, Glucose 2.4 g and HEPES 10 g, pH=7.05) to form a calcium phosphate-DNA suspension which is added into 293F or CHO cells (logarithmic growth phase). The supernatant is collected 5-7 days after the transfection. After filtration through a 0.45 μm filter, the supernatant is added to the affinity chromatography gel column (Protein A) which is washed with binding buffer (12.15 g Tris dissolved in ddH$_2$O, pH=7.5, adding 8.78 g NaCl). Then it is eluted by eluent (7.5 g glycine dissolved in ddH$_2$O, pH=3.5, adding 8.78 g NaCl). The eluted fraction, which is the bispecific antibody as shown in FIG. 1, is neutralized with 1 M Tris-HCl (pH 9.0).

Example 2 Enzyme-Linked Immunosorbent Assay (ELISA)

The human p185 and VEGF proteins are coated into 96 well plates for 16 hours and being incubated with PBS buffer containing 1% bovine serum albumin (BSA) at 37° C. for 2 hours. After washing with PBST, it is incubated with the commercially available p185 and VEGF antibody as well as the antibody of the present invention at 37° C. for 2 hours. Following by the PBST washing, anti-human IgG Fab antibody is added for 1 hour. After washing with PBST, tetramethyl benzidine is added for 5 minutes to terminate the reaction. The affinity is measured with the absorbance at 450 nm.

The ELISA results are shown in FIG. 2. The results suggest that the bispecific antibody targeting both human p185 and VEGF has high affinity with human p185 (FIG. 2(a)), VEGF (FIG. 2(b)), p185-VEGF (FIG. 2(c)), and VEGF-p185 (FIG. 2(d)).

Example 3 Western Blotting Assay (1) The Recognition of VEGF by the Bispecific Antibody The HUVEC cells which are morphological health and with the fusion rate of 80% are collected. After centrifugation, the cell lysate is added. The cell lysate is incubated at 95° C. for 10 minutes and is separated by polyacrylamide gel electrophoresis. The protein is transferred into the nitrocellulose membrane (NC membrane) and blocked with 5% milk at room temperature for 1 hour. The bispecific antibody, commercially available VEGF or 1-actin antibody is added and incubated at room temperature for 1 hour. After washing with PBST, the antibody with horseradish peroxidase is added and incubated for 1 hour at room temperature. After washing with PBST, the chemiluminescent reagent is used for developing in the darkroom.

(2) The Recognition of p185 by the Bispecific Antibody

The MDA-MB-453 cells which are morphological health and with the fusion rate of 80% are collected. After centrifugation, the cell lysate is added. The cell lysate is incubated at 95° C. for 10 minutes and is separated by polyacrylamide gel electrophoresis. The protein is transferred into the nitrocellulose membrane (NC membrane) and blocked with 5% milk at room temperature for 1 hour. The bispecific antibody, commercially available p185 or β-actin antibody is added and incubated at room temperature for 1 hour. After washing with PBST, the antibody with horseradish peroxidase is added and incubated for 1 hour at room temperature. After washing with PBST, the chemiluminescent reagent is used for developing in the darkroom.

Figure 3A:
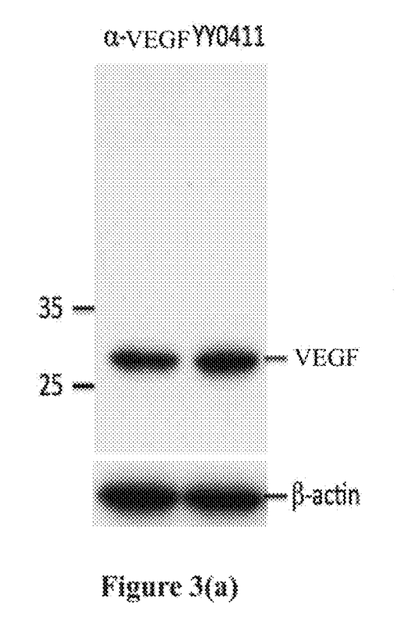
FIG. 3(a) shows the recognition at the protein level for VEGF.
Figure 3B:
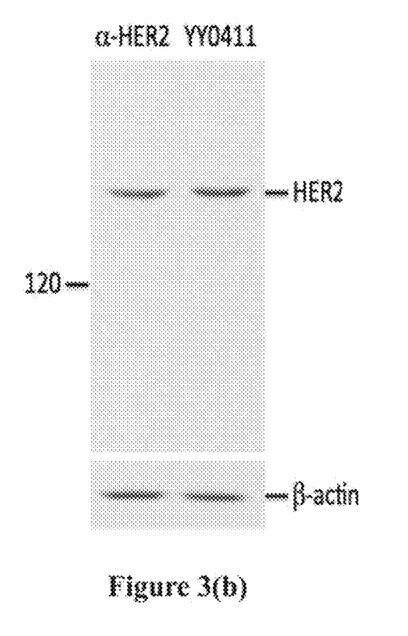
FIG. 3(b) shows the recognition at the protein level for p185.

The results of the western blotting assay are shown in FIG. 3. The results indicate that the bispecific antibody targeting both human p185 and VEGF efficiently recognizes p185 (FIG. 3(b) and VEGF (FIG. 3(a).

Example 4 Cell Proliferation Assay

Cells, including HUVEC cells, human lung cancer cells, human breast cancer cells, and human gastric cancer cells, are seeded in the 96-well plate and cultured in medium containing 0.5% fetal bovine serum overnight. Each cell lines include five groups, i.e., control group, commercially p185 antibody group, commercially VEGF antibody group, commercially p185 and VEGF antibody group, and the bispecific antibody). Cells are cultured for 72 hours. The proliferation of cells is detected through commercially available cell proliferation assay kit (CCK8 Kit).

Figure 4:
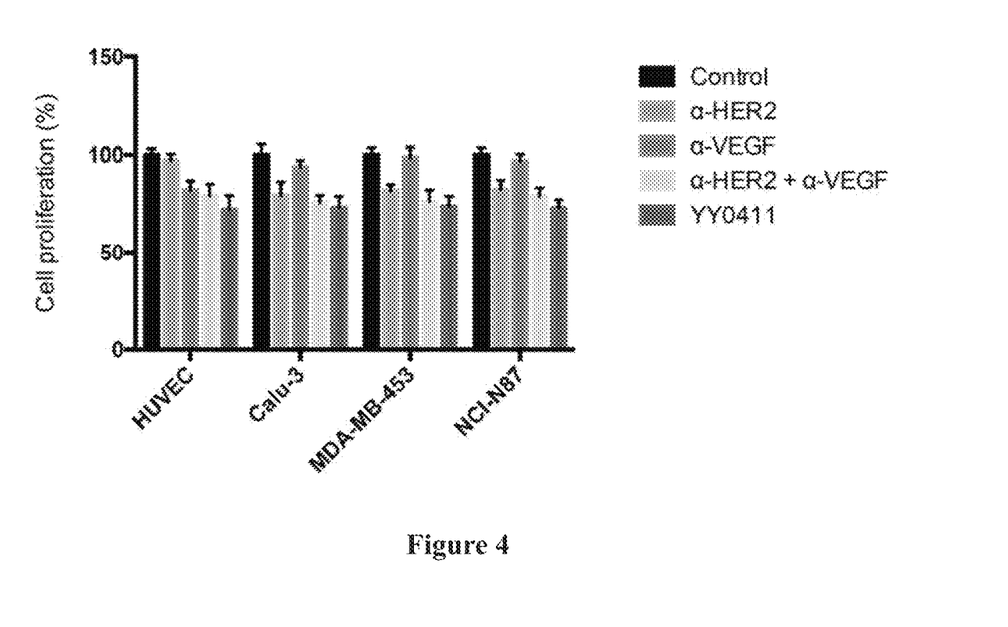
FIG. 4 shows that the bispecific antibody of the present invention, having the light chain sequence of SEQ ID NO: 1 and the recombinant heavy chain sequence of SEQ ID NO: 2 that targets human p185 and VEGF, inhibits the proliferation of vascular endothelial cells, human lung cancer cells, human breast cancer cells and human of gastric cancer cells (detection time: 96 hours after administration).

The results of cell proliferation test are shown in FIG. 4. The results suggest that the bispecific antibody targeting both human p185 and VEGF effectively inhibits the proliferation of HUVEC cells, human lung cancer cells, human breast cancer cells, and human gastric cancer cells.

Example 5 T Cell Stimulation Test

The suspension of T lymphocyte is added into a 96-well plate. The test includes two groups which are added with the medium and the bispecific antibody. Cells are cultured for 72 hours. The enzyme-linked immunosorbent assay (ELISA) kit is used to detect the concentration of IFN-γ.

Figure 5:
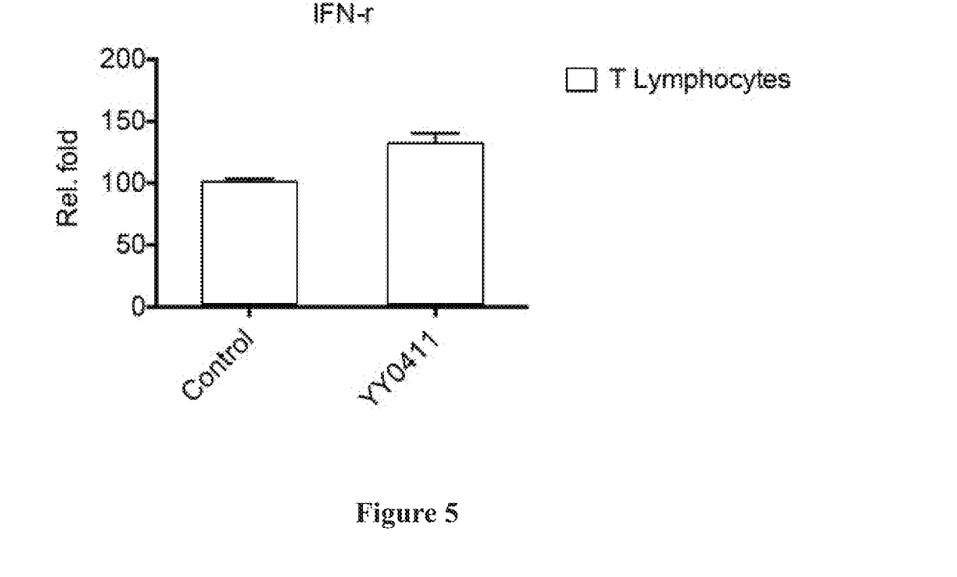
FIG. 5 shows that the bispecific antibody of the present invention, having the light chain sequence of SEQ ID NO: 1 and the recombinant heavy chain sequence of SEQ ID NO: 2 that targets human p185 and VEGF, promotes IFN-γ secretion by human T lymphocytes.

The results of T cell stimulation test are shown in FIG. 5. The results indicate that the bispecific antibody targeting both human p185 and VEGF promotes the IFN-γ expression of T lymphocytes.

Comparative Example 1

The connection of conventional p185 antibody and conventional VEGF antibody with the same procedure of the present invention is not able to simultaneously target both p185 and VEGF. Some connections are with low expression, while some connections could not be expressed due to the spatial structure. Some connections which are able to express are with decreased binding ability with p185 and/or VEGF.

We claim:

1. A bispecific antibody that simultaneously binds human p185 and VEGF comprising two identical antibody light chains, and two identical antibody heavy chains, wherein each antibody light chain comprises the amino acid sequence of SEQ ID NO:1 and wherein each antibody heavy chain comprises the amino acid sequence of SEQ ID NO:2.

* * * * *